United States Patent [19]

Groeger et al.

[11] Patent Number: 5,120,652

[45] Date of Patent: Jun. 9, 1992

[54] **SUBSTANTIALLY PURIFIED N-ACYL-L-PROLINE ACYLASE FROM *COMAMONAS TESTOSTERONI* DSM 5416 AND *ALCALIGENES DENITRIFICANS* DSM 5417**

[75] Inventors: Ulrich Groeger, Aschaffenburg; Wolfgang Leuchtenberger, Bielefeld; Karlheinz Drauz, Freigericht, all of Fed. Rep. of Germany

[73] Assignee: Degussa AG, Fed. Rep. of Germany

[21] Appl. No.: 580,929

[22] Filed: Sep. 6, 1990

[30] Foreign Application Priority Data

Sep. 6, 1989 [DE] Fed. Rep. of Germany ....... 3929570

[51] Int. Cl.$^5$ ............................ C12N 9/80; C12N 1/00
[52] U.S. Cl. .................................... 435/228; 435/829; 435/822

[58] Field of Search ............. 435/228, 829, 822

[56] References Cited

FOREIGN PATENT DOCUMENTS

| | | | |
|---|---|---|---|
| 55-7015 | 1/1980 | Japan | 435/228 |
| 64-5488 | 1/1989 | Japan | 435/228 |
| 64-74987 | 3/1989 | Japan | 435/228 |

*Primary Examiner*—Douglas W. Robinson
*Assistant Examiner*—Mike Meller
*Attorney, Agent, or Firm*—Cushman, Darby & Cushman

[57] ABSTRACT

A substantially purified N-acyl-L-proline-acylase from *Comamonas testosteroni* DSM 5416 and *Alcaligenes denitrificans* DSM 5417. The enzyme is useful for the synthesis of L-proline from various N-acyl-L-proline derivatives.

1 Claim, No Drawings

SUBSTANTIALLY PURIFIED N-ACYL-L-PROLINE ACYLASE FROM *COMAMONAS TESTOSTERONI* DSM 5416 AND *ALCALIGENES DENITRIFICANS* DSM 5417

The present invention relates to a novel enzyme which catalyses reactions of the following type:

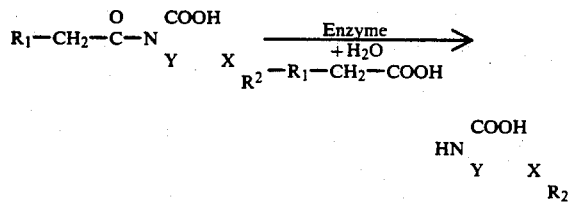

The new enzyme is thermostable and results in an especially good conversion when $R_1=H$, $X=CH$ and $R_2=H$, when $R_1=Cl$, $X=CH$ and $R_2=H$, when $R_1=H$ and $X-R_2=S$, $R_1=Cl$ and $X-R_2=S$, when $R_1=H$, $X=CH$, $R_2=H$ and $Y=S$ and when $R_1=Cl$, $X=CH$, $R_2=H$ and $Y=S$.

BACKGROUND OF THE INVENTION

A proline acylase (N-acyl-L-proline amido hydrolase) from a pseudomonas strain is described in Biochimica et Biophysica Acta, 744 (1983), pp. 180-188, Elsevier Biomedical Press. That enzyme is very rapidly inactivated at a temperature as low as 50° C. However, enzymes are required for industrial use which have a high degree of stability. It is especially advantageous to carry out the reaction at elevated temperatures, which considerably raise the reaction speed and the solubility of the substrates, but this requires an enzyme which can withstand such temperatures.

SUMMARY OF THE INVENTION

The object of the present invention is to provide an enzyme which is considerably more thermostable. The invention also provides a process of the type described above, using the aforesaid enzyme.

THE CHARACTERISTICS OF THE ENZYME

The enzyme of the invention is characterized by the following properties:

1) Reactivity

It splits the acetyl group from N-acetyl-L-proline, creating acetic acid and L-proline as the final products and it condenses acetic acid and L-proline, creating N-acetyl-L-proline and water as final products:

2) Substrate specificity

It hydrolyzes N-acetyl-L proline, N-chloroacetyl-L-proline, N-formyl-L-proline, N-propionyl-L-proline, N-butyryl-L-proline, N-valeryl-L-proline, N-caproyl-L-proline, N-acetyl-L-4-hydroxyproline, N-chloroacetyl-L-thiazolidine-4-carboxylic acid, N-chloroacetyl-L-thiazolidine-2-carboxylic acid, N-chloroacetyl-L-pipecolic acid, N-benzyloxycarbonyl-glycyl-L-proline, glycyl-L-proline, N-acetyl-L-alanine, N-chloroacetyl-L-methionine and N-chloroacetyl-L-valine;

3) Optimum pH

The optimum pH is $6.8\pm0.5$;

4) pH stability

It exhibits good stability at 22° C. over a period of 3 weeks in a pH range between pH 7.0 and pH 10.0:

5) Optimum temperature

The optimum temperature is 65° C. at a pH of 7.5;

6) Temperature resistance

No loss of activity can be detected at 70° C. and pH 7.5 after 30 minutes of incubation;

7) Influences of inhibitors and activators

In particular, 1,10-phenanthroline, 2-mercaptoethanol, 4-chloromercuribenzoate, 4-hydroxymercuribenzoate, $Hg^{2+}$, $Cu^{2+}$, $Fe^{2+}$, $Fe^{3+}$, $Sn^{2+}$, $Zn^{2+}$ and $PO_4^{3-}$ exhibit an inhibiting action and $Co^{2+}$ and $Zn^{2+}$ an activating action on the apoenzyme;

8) Molecular weight

The molecular weight is $380,000\pm40,000$ daltons;

9) Subunits

The molecule consists of 8 equally large subunits with $45,000\pm6,000$ daltons each;

10) $K_M$ value

The $K_M$ value for the substrate N-acetyl-L-proline is 5 mM (30° C., 0.1 M tris-HCl buffer, pH 7.0).

SYNTHESIS OF THE ENZYME

The N-acyl-L-proline acylase of the invention can be obtained by cultivating the Comamonas testosteroni strain DSM 5416 or the Alcaligenes denitrificans strain DSM 5417. These two strains were deposited on December 19, 1988 in the Deutsche Sammlung von Mikroorganismen und Zellkulturen GmbH (German Collection of Microorganisms and Cell Cultures) (DSM) in Braunschweig, Federal Republic of Germany.

The following characteristics show that the strain DSM 5416 belongs to the species Comamonas testosteroni:

It grows in gram-negative rods 0.5–0.7 μm wide and 1.5–3.0 μm long which can be moved by means of more than one polar flagellum and forms no spores. The cells are lysed by 3 % KOH. Aminopeptidase (Cerny)-, oxidase-, catalase- and phenylalanine deaminase reaction are positive, lecithinase- and urease reaction are negative. The growth is strictly aerobic, positive at pH 5.6 on Mac-Conkey agar and Simmons citrate agar, negative at 37° C. and 41° C., SS agar and cetrimide agar. Pigment formation, ONPG-, ADH- and VP reaction are negative. Nitrate reduction is positive, denitrification is negative. Starch, gelatins, casein, DNA, Tween 80 and asculine are not hydrolyzed. Vitamins are required for growth, the tyrosine degradation is positive. The following substrates are utilized for growth as carbon source and energy source: gluconate, glycerol, pyruvate, L-lactate, malate, adipate, laevulinate, mucate, D-tartrate, sebacinate, 2-ketoglutarate, acetate, propionate, butyrate, N-acetyl-L-proline, L-proline, L-leucine, L-aspartate, norleucine and τ-aminobutyrate. No growth on arabinose, glucose, fructose, lactose, maltose, mannose, saccharose, xylose, mannite, 2-ketogluconate, N-acetylglucose amine, caproate, citrate, glycolate, malonate, phenylacetate, L-arginine, L-histidine, L-serine and L-tryptophane.

The following characteristics show that the strain DSM 5417 belongs to the species Alcaligenes denitrificans:

It grows in gram-negative rods 0.5–0.6 μm wide and 1.0–2.0 μm long which can be moved by means of peritrichally arranged flagella and forms no spores. The cells are lysed by 3% KOH. Aminopeptidase (Cerny)-, oxidase- and catalase reaction are positive, phenylalanine deaminase-, lecithinase- and urease reaction are negative. The growth is aerobic, positive at pH 5.6 at 37° C. on MacConkey agar, SS agar and Simmons citrate agar, negative at 41° C. and on cetrimide agar.

Pigment formation, ONPG-, ADH- and VP reaction are negative. Nitrate reduction and denitrification are positive. Poly-$\beta$-hydroxybutyric acid (PHB) is formed as storage substance. Starch, gelatins, casein, DNA, Tween 80 and asculine are not hydrolyzed. The tyrosine degradation is positive. The following substrates are utilized for growth as carbon source and energy source: Acetate, adipate, caproate, citrate, L-lactate, malate, propionate, phenylacetate, azelate, gluconate, N-acetylglucosamine, N-acetyl-L-proline, L-proline, L-aspartate and L-glutamate. No growth on arabinose, glucose, fructose, mannose, maltose, xylose, mannite, 2-ketogluconate, glycolate, laevulinate, malonate, oxalate, meso-tartrate, itaconate, pimelate, sebacinate, suberate, L-alanine and L-serine.

The microorganisms can be preserved as lyophilized culture, by freezing at $-80°$ C. or in liquid nitrogen at $-196°$ C.

Working cultures are maintained on slant agar tubes (casein peptone - soybean flour agar of the firm Merck AG, Darmstadt, Federal Republic of Germany).

In order to obtain the N-acyl-L-proline acylase of the invention, Comamonas testosteroni DSM 5416 or Alcaligenes denitrificans DSM 5417 is aerobically cultivated in an aqueous nutrient medium which contains a source for carbon, nitrogen, mineral salts and N-acetyl-L-proline as inductor, and, when using Comamonas testosteroni DSM 5416, a vitamin source in addition, e.g. in complex form as yeast extract, at an initial pH between 6.0 and 8.0 and a temperature between 25° C. and 35° C., the cell mass is separated and the enzyme isolated from the cells.

The enzyme can be obtained in larger amounts, for example, by cultivating Comamonas testosteroni DSM 5416 or Alcaligenes denitrificans DSM 5417 in a known manner in a bioreactor of the desired size.

The following are important for successful cultivation:

Good aeration (aerobic organism);

An initial pH of the nutrient medium between 6.0 and 8.0;

The presence of N-acetyl-L-proline in the nutrient medium for the induction of the enzyme (0.06% to 0.1% by weight);

The presence of vitamins (e.g. in complex form as yeast extract).

The enzyme can be obtained after maceration of the cells by a combination of known methods of enzyme purification. The enzyme can be used to obtain L-proline from N-acetyl-L-proline, N-chloroacetyl-L-proline, N-acetyl-D,L-proline or N-chloroacetyl-D,L-proline. In addition, the enzyme can be used to produce N-acetyl-L-proline, N-propionylL-proline and N-butyryl-L-proline from L-proline and the respective carboxylic acid.

DETAILED DESCRIPTION OF PREFERRED EMBODIMENTS

The invention is illustrated in more detail in the following examples:

EXAMPLE 1

The search for producers of N-acyl-L-proline acylase

The materials tested included 3 soil samples suspended in 0.9% (w/v) NaCl as well as one undiluted sample from a sewage treatment plant. 1 ml samples of the respective suspensions and 1 ml of the undiluted sample from the sewage treatment plant were injected into 50 ml samples of the nutrient medium. The nutrient medium had the following composition:

| | |
|---|---|
| N-acetyl-L-proline | 5 g |
| Yeast extract | 0.1 g |
| $K_2HPO_4$ | 2 g |
| NaCl | 1 g |
| $MgSO_4 \cdot 7 H_2O$ | 0.3 g |
| $CaCl_2 \cdot 2 H_2O$ | 0.1 g |
| Trace-element solution | 1 ml |
| Demineralized $H_2O$ to dilute to | 1 liter |
| pH | 5.6 and 7.4 |

The trace-element solution had the following composition:

| | |
|---|---|
| $FeCl_3 \cdot 6 H_2O$ | 250 mg |
| $ZrCl_2$ | 75 mg |
| $H_3BO_3$ | 30 mg |
| $CuSO_4 \cdot 5 H_2O$ | 20 mg |
| $MnCl_2 \cdot 4 H_2O$ | 20 mg |
| $CoCl_2 \cdot 6 H_2O$ | 14 mg |
| $(NH_4)_6Mo_7O_{24} \cdot 4 H_2O$ | 10 mg |
| 0.01N HCl sufficient to dilute to | 100 ml |
| pH | ~1.7. |

50 ml of the nutrient medium were added to 500 ml Erlenmeyer flasks (with top and 4 lateral baffles) and autoclaved. The trace-element solution was sterilized by filtration and added to each flask after it cooled. The flasks were inoculated as indicated above and aerobically incubated in a rotary agitator at 200 rpms for 3 days. Densely grown-over batches were diluted in the usual manner with sterile 0.% (w/v) NaCl solution and plated out onto agar plates (nutrient medium with 1.2% (w/v) agar-agar, pH 5.6). The agar plates were incubated for 5 days at 30° C. and colonies which grew well were individualized and transferred a total of 4 to 5 times onto the same medium.

Strains which appeared uniform according to the colony morphology and the microscopic image were then cultivated in 100 ml liquid medium (500 ml Erlenmeyer flask with top and 4 lateral baffles) at 30° C. on a rotary agitator machine at 200 rpms. The culture medium had the following composition:

| | |
|---|---|
| N-acetyl-L-proline | 4 g |
| $(NH_4)_2SO_4$ | 2 g |
| Yeast extract | 1 g |
| $K_2HPO_4$ | 2 g |
| $MgSO_4 \cdot 7 H_2O$ | 0.3 g |
| $CaCl_2 \cdot 2 H_2O$ | 0.1 g |
| NaCl | 1 g |
| Trace-element solution | 1 ml |
| Demineralized $H_2O$ sufficient to dilute to | 1 liter |
| pH | 7.0 |

After 24 to 48 hours, the cell-containing nutrient medium was centrifuged (15 min., 4,500 g in a cooling centrifuge), the cells were washed twice with 0.9% (w/v) NaCl solution and resuspended in 10 ml 0.1 M tris-HCl buffer, pH 7.0.

The microorganisms of this suspension were macerated by ultrasound treatment (Sonifier-Cell Disrupter B-30 of the firm Branson Sonic Power Co., Danbury, Connecticut, USA) (2 minutes pulsating, corresponding to 1 minute of pure ultrasonic radiation. The cell fragments and non-macerated cells were centrifuged in a cooled centrifuge 30 minutes at 40,000 g and 5° C. The clear supernatant (=crude extract) was used in an enzyme test.

The standard reaction batch for determining the enzyme activity was composed as follows:

| | | |
|---|---|---|
| 30 mM | N-acetyl-L-proline in 0.1 M tris-HCl buffer, adjusted to pH 7.0 | 1.0 ml |
| 0.1 M | Tris-HCl buffer pH 7.0 | 1.95 ml |
| | Crude extract | 0.05 ml |

The reaction was started by adding crude extract and the reaction batches customarily incubated for 10 minutes at 30° C. The incubation time and the amount of crude extract were selected so that the linearity range of the enzymatic reaction and of the subsequent proline detection were not exceeded.

Detection of the reaction product L-proline by means of ninhydrin reaction (according to Yaron and Mlynar [sic], Biochem. Biophys. Res. Commun. 32 (4), pp. 658–663 (1968)).

The enzymatic reaction was interrupted by pipetting 50 μl of the enzyme sample into 1.25 ml 100% acetic acid. Subsequently, 0.45 ml 0.1 M tris-HCl buffer pH 7.0 and 1.25 ml ninhydrin reagent (3 g ninhydrin dissolved by heating in a mixture of 60 ml 100% acetic acid and 40 ml 6 M phosphoric acid) were added. The ninhydrin reagent was freshly prepared daily. The test tubes were loosely closed with screw-on caps, incubated 30 minutes at 100° C. and subsequently cooled down in an ice bath.

The L-proline, liberated by the enzymatic hydrolysis, forms a red dye with ninhydrin at 100° C. The absorption of the red dye was measured in a spectrophotometer at 480 nm relative to a control batch without crude extract (=substrate blank). The concentration of the L-proline produced was determined using a straight calibration line with L-proline in a range of 5 to 100 nmoles per 50 μl specimen. The enzyme activity was indicated in international units; thus, one unit (U) corresponded to an amount of 1 μmole L-proline produced per minute.

The protein determination was carried out with a protein-determination kit of the firm Pierce Chemical Co., Rockford, Illinois, USA, according to Bradford, Anal. Biochem. 72, pp. 248–254 (1976).

TABLE 1

Formation of N-acyl-L-proline acylase by means of various screened bacterial strains

| Strain | Spec. activity (U/mg) |
|---|---|
| B-A1 (DSM 5417) | 0.64 |
| B-A2 | 0.34 |
| B-A3 | 0.55 |
| B-B | 0.59 |
| B-K (DSM 5416) | 2.98 |
| B-L | 0.19 |
| B-M | 0.09 |
| Sub 4 | 0.42 |
| Sub 5 | 0.16 |
| Sub 6 | 0.41 |

As Table 1 shows, strain B-K exhibited by far the highest activity in the test method described and was therefore used for the production of the enzyme. The strains B-K and B-AI were identified by the Deutsche Sammlung von Mikroorganismen und Zellkulturen GmbH [German Collection of Microorganisms and Cell Cultures] (DSM) in Braunschweig, Federal Republic of Germany, as *Comamonas testosteroni* and *Alcaligenes denitrificans*.

EXAMPLE 2

Growth and acylase formation of Comamonas testosteroni DSM 5416.

a) Growth and acylase formation on various carbon sources

*Comamonas testosteroni* DSM 5416 was, as was described in Example 1, multiplied in a culture medium, the cells macerated by ultrasonification and the specific activity of the N-acyl-L-proline acylase determined. The carbon source of the culture medium with a concentration of 4 g/l was varied and the influence on growth and acylase formation determined.

TABLE 2

Influence of various carbon sources on the growth and the specific activity of N-acyl-L-proline acylase

| C source* | Growth ($OD_{600}$) | Spec. activity (U/mg) |
|---|---|---|
| N-acetyl-L-proline | 6.0 | 2.26 |
| Acetate | 2.3 | <0.01 |
| Propionate | 1.9 | <0.01 |
| Butyrate | 1.8 | <0.01 |
| Pyruvate | 2.4 | <0.01 |
| Lactate | 3.0 | <0.01 |
| Malate | 3.4 | <0.01 |
| Glycerol | 1.1 | <0.01 |
| L-aspartate | 2.0 | <0.01 |
| L-leucine | 2.6 | <0.01 |
| L-proline | 3.9 | <0.01 |

*No growth on arabinose, glucose, fructose, lactose, maltose, mannose, saccharose, xylose, citrate, phenylacetate, L-arginine, L-histidine, L-serine and L-tryptophane As can be seen from Table 2, the N-acyl-L-proline acrylase was only formed by means of Comamonas testosteroni DSM 5416 during growth on N-acetyl-L-proline as the carbon source. No enzyme activity was observed during growth on other carbon sources.

b) Growth and acylase formation at various starting pH's

The pH was varied in a range of 6.0–8.0 in steps of 0.5 units in the culture medium as described in Example 1 but with 2 g/l N-acetyl-L-proline. After an incubation time of 17.5 hours, the pH of the medium, the growth, as observed by measurement of the optical density at 600 nm, and the specific activity of the N-acyl-L-proline acylase were determined.

TABLE 3

Dependence of the growth and of the formation of N-acyl-L-proline acylase on the pH of the culture medium

| Initial pH | Final pH | Growth ($OD_{600}$) | Spec. activity (U/mg) |
|---|---|---|---|
| 6.0 | 8.00 | 3.55 | 1.52 |
| 6.5 | 8.05 | 3.78 | 1.31 |
| 7.0 | 8.00 | 3.80 | 1.36 |
| 7.5 | 8.06 | 3.53 | 1.34 |
| 8.0 | 8.00 | 3.88 | 0.58 |

Table 3 shows that the final pH and the growth are not influenced by the initial pH of the culture medium. In the pH range 6.0–7.5, even the specific activity of the acylase is not influenced to significant degree, whereas, at pH 8.0, only approximately one third of the enzyme activity is achieved.

c) Growth and acylase formation at various concentrations of N-acetyl-L-proline

The concentration of N-acetyl-L-proline was varied in a range of 1 g/l –5 g/l in steps of 1 g/l in the culture medium as described in Example 1. After an incubation time of 24 hours, the growth and the specific activity of the N-acyl-L-proline acylase were determined.

TABLE 4

Dependence of the growth and of the formation of N-acyl-L-proline acylase on the N-acyl-L-proline concentration of the culture medium

| N-acetyl-L-proline (g/l) | Growth (OD$_{600}$) | Spec. activity (U/mg) |
| --- | --- | --- |
| none | 0.39 | n.d. |
| 1 | 1.95 | 1.33 |
| 2 | 3.16 | 1.36 |
| 3 | 4.32 | 1.77 |
| 4 | 5.42 | 1.84 |
| 5 | 5.68 | 0.94 | n.d. = not determined

Table 4 shows that the cell density achieved was dependent on the amount of N-acetyl-L-proline used. Only slight growth can be recorded without N-acetyl-L-proline, which can be attributed to the yeast extract present in the culture medium. As the N-acetyl-L-proline concentration increased, the specific activity of the acylase rose and reached an optimum at 4 g/l N-acetyl-L-proline.

d) Growth and acylase formation at various concentrations of $(NH_4)_2SO_4$

The concentration of $(NH_4)_2SO_4$ was varied in a range of 1 g/l –5 g/l in steps of 1 g/l in the culture medium as described in Example 1. After an incubation time of 23 hours, the growth and the specific activity of the N-acyl-L-proline acylase were determined.

TABLE 5

Dependence of the growth and of the formation of N-acyl-L-proline acylase on the $(NH_4)_2SO_4$ concentration of the culture medium

| $(NH_4)_2SO_4$ (g/l) | Growth (OD$_{600}$) | Spec. activity (U/mg) |
| --- | --- | --- |
| without | 4.82 | 0.38 |
| 1 | 5.24 | 1.71 |
| 2 | 5.67 | 1.91 |
| 3 | 5.47 | 1.53 |
| 4 | 5.44 | 1.59 |
| 5 | 5.47 | 1.32 |

Table 5 shows that the growth and the formation of the acylase were optimum at an $(NH_4)_2SO_4$ concentration of 2 g/l. $(NH_4)_2SO_4$ obviously aided the formation of the acylase, since without $(NH_4)_2SO_4$ the specific activity of the acylase was only 20% of the optimum value whereas the achieved cell density was not significantly less. In this instance, the yeast extract present in the culture medium and the L-proline released from the N-acetyl-L-proline functioned as nitrogen source for the growth of the cells.

e) Growth and acylase formation at various concentrations of yeast extract

The concentration of yeast extract was varied in a range of 1 g/l –5 g/l in steps of 1 g/l in the culture medium as described in Example 1. After an incubation time of 24 hours, the growth and the specific activity of the N-acyl-L-proline acylase were determined.

TABLE 6

Dependence of the growth and of the formation of N-acyl-L-proline acylase on the concentration of yeast extract of the culture medium

| Yeast Extract (g/l) | Growth (OD$_{600}$) | Spec. activity (U/mg) |
| --- | --- | --- |
| without | 0.02 | n.d.* |
| 1 | 6.11 | 2.14 |
| 2 | 7.03 | 1.30 |
| 3 | 7.55 | 1.30 |
| 4 | 8.05 | 1.26 |
| 5 | 8.82 | 1.46 |

*n.d. = not determined

Table 6 shows that the formation of acylase was optimum at a concentration of yeast extract of 1 g/l whereas the achieved cell density rose with increasing concentration of yeast extract. The cells did not grow without yeast extract, which indicates complex nutrient requirements of the strain.

f) Growth and acylase formation with simultaneous supply of acetate and N-acetyl-L-proline to the nutrient medium The N-acetyl-L-proline concentration was reduced to 0.2 to 1.0 g/l in the culture medium as described in Example 1 and 4 g/l Na acetate were additionally added. After an incubation time of 34 hours, the growth and the specific activity of the N-acyl-L-proline acylase were determined.

TABLE 7

Growth and induction of N-acyl-L-proline acylase with simultaneous supply of Na acetate and N-acetyl-L-proline in the nutrient medium

| N-acetyl-L-proline (g/l) | Growth (OD$_{600}$) | Spec. activity (U/mg) |
| --- | --- | --- |
| without | 2.35 | <0.01 |
| 0.2 | 2.27 | 0.53 |
| 0.4 | 2.90 | 0.79 |
| 0.6 | 2.75 | 1.41 |
| 0.8 | 3.04 | 1.70 |
| 1.0 | 3.12 | 1.55 |

Table 7 shows that the acylase was only formed in the presence of N-acetyl-L-proline but, at the same time, it was not repressed by acetate. This permits obtaining a sufficiently large amount of biomass by means of the simultaneous supplying of acetate and N-acetyl-L-proline as carbon sources. 0.6 g/l of the inductor was sufficient to adequately induce the formation of acylase.

g) Growth and acylase formation with the addition of N-acetyl-L-proline to the nutrient medium in the late exponential growth phase The method described above under f) was followed. However, the inductor, N-acetyl-L-proline, was not added to the nutrient medium until the late exponential growth phase after an incubation time of 12 hours. The nutrient medium was incubated 24 hours further and the growth and the specific activity of the N-acyl-L-proline acylase determined.

TABLE 8

Growth and induction of N-acyl-L-proline acylase with the addition of N-acetyl-L-proline in the late exponential growth phase

| N-acetyl-L-proline (g/l) | Growth (OD$_{600}$) | Spec. activity (U/mg) |
| --- | --- | --- |
| without | 1.92 | <0.01 |
| 0.2 | 2.22 | 0.50 |
| 0.4 | 2.28 | 0.63 |
| 0.6 | 2.76 | 0.96 |

TABLE 8-continued

Growth and induction of N-acyl-L-proline acylase
with the addition of N-acetyl-L-proline in the
late exponential growth phase

| N-acetyl-L-proline (g/l) | Growth (OD$_{600}$) | Spec. activity (U/mg) |
|---|---|---|
| 0.8 | 2.95 | 0.67 |
| 1.0 | 2.88 | 1.08 |

A comparison of Tables 7 and 8 shows that 0.6 g/l N-acetyl-L-proline were sufficient in an acetate-containing nutrient medium to sufficiently induce the formation of acylase. Therefore, it is advantageous to add the inductor to the nutrient medium before the inoculation.

h) Growth and acylase formation with simultaneous supply of Na acetate and various N-acetyl- and N-chloroacetyl amino acids in the nutrient medium The method described above under f) was followed. In addition to N-acetyl-L-proline, various N-acetyl- and N-chloroacetyl amino acids were added to the nutrient medium in a concentration of 1 g/l. After an incubation time of 24 hours, the growth and the specific activity of the N-acyl-L-proline acylase were determined.

TABLE 9

The influence of various N-acetyl- and N-chloroacetyl amino acids on the growth and the acylase formation

| Inductor | Growth (OD$_{600}$) | Spec. activity (U/mg) |
|---|---|---|
| without | 2.60 | <0.01 |
| Ac-L-Ala | 2.28 | <0.01 |
| Ac-L-Pro | 3.46 | 1.34 |
| ClAc-L-Met | 2.19 | <0.01 |
| ClAc-L-Val | 2.50 | <0.01 |
| ClAc-L-Leu | 2.65 | <0.01 |
| ClAc-L-Phe | 2.89 | <0.01 |
| ClAc-L-Tyr | 2.76 | <0.01 |

As can be seen from Table 9, of the N-acetyl- and N-chloroacetyl amino acids tested, only N-acetyl-L-proline induced acylase formation.

EXAMPLE 3

Purification of N-acyl-L-proline acylase a) Cultivation of Comamonas testosteroni DSM 5416 and obtaining crude extract Comamonas testosteroni DSM 5416 was cultivated on slant agar (casein - peptone / soybean meal - peptone agar of the firm Merck AG, Darmstadt, FRG) and floated off with 4.5 ml sterile 0.9% (w/v) NaCl solution per slant agar tube. The cell suspension obtained in this manner functioned as inoculum for 4 Erlenmeyer flasks (2 l with 4 baffles), each of which contained 500 ml culture medium as described in Example 1. The Erlenmeyer flasks were incubated 21 hours on a rotary agitator at 30° C. and 100 rpms and the cells, as was described in Example 1, harvested, washed, resuspended in 30 ml 0.1 M tris-HCl buffer pH 7.0, and macerated by ultrasound.

b) 70° C. heat precipitation

The cell-free crude extract (38.5 ml) was incubated 30 minutes in a water bath at a temperature of 70° C. The protein precipitated after this time was separated by centrifugation (30 minutes at 40,000 g and 5° C.).

c) Concentration by filtration

The supernatant of the 70° C. heat precipitation (34.5 ml) was concentrated by filtration via a flat membrane with an exclusion limit of 100,000 daltons (YM 100) in an agitator cell (model 8050 of the firm W. R. Grace Co., Amicon Division, Danvers, USA) at a pressure of 4 bars under nitrogen.

d) Fast protein liquid chromatography (FPLC) on mono Q

The solid material separated by filtration (4.5 ml) was applied onto a 0.5×5 cm Mono Q column (firm Pharmacia / LKB, Uppsala, Sweden) and chromatographed at a flow of 1 ml/min. The anion exchanger was equilibrated before the application of the specimen with a 0.1 M tris-HCl buffer pH 7.0. Elution was carried out with a linear NaCl gradient rising within 20 ml from 0 to 0.4 M in 0.1 M tris-HCl buffer pH 7.0. The elution of the enzyme took place at 0.2–0.25 M NaCl. A total of 14 operations were carried out at a specimen volume of 0.2 ml per operation. The active fractions were combined and frozen at −20° C.

TABLE 10

Purification scheme for N-acyl-L-proline acylase

| Purification step | Volume (ml) | Total protein (mg) | Total activity (U) | Yield (%) | Spec. activity (U/mg) | enrichment (times) |
|---|---|---|---|---|---|---|
| Crude extract | 38.5 | 472.0 | 754.7 | 100 | 1.60 | 1 |
| 70° C. heat precipitation | 34.5 | 86.6 | 618.0 | 82 | 7.14 | 4.5 |
| Concentration (Amicon agitator cell with YM-100 membrane, 100,000 d) | 4.5 | 56.2 | 585.6 | 78 | 10.42 | 6.5 |
| FPLC-Mono Q | 27.5 | 4.4 | 374.7 | 50 | 85.16 | 53.2 |

EXAMPLE 4

Dependence of the reaction speed on the pH

The reaction speed of the hydrolytic splitting of acetic acid from the compound N-acetyl-L-proline in the presence of N-acyl-L-proline acylase was determined as a function of the pH of the reaction mixture. The test batch had the following composition:

| 10 mM | N-acetyl-L-proline in the 0.1 M buffer indicated below | 2.95 ml |
|---|---|---|
| | Acylase | 0.05 ml |

Before the start of the reaction by the addition of acylase, the pH was adjusted in several samples of the substrate-buffer mixture in the range from 4.0 to 5.0 in 0.1 M acetic acid/NaOH buffer, in the range from 5.0 to 6.0 in 0.1 M Na citrate/NaOH buffer, in the range from 6.0 to 7.5 in 0.1 M K$_2$HPO$_4$/ KH$_2$PO$_4$ buffer, in the range from 6.2 to 9.0 in 0.1 M tris-HCl buffer and in the range from 9.0 to 10.0 in 0.1 m Na$_2$CO$_3$/ NaHCO$_3$ by means of the addition of 2 N NaOH to the desired pH. After 10 minutes reaction time at 30° C., the enzyme activity was determined by means of ninhydrin detection of the L-proline formed.

The optimum of the reaction speed in the tris-HCl buffer was in the pH range between 6.2 and 7.2 and in the potassium phosphate buffer the pH optimum was in the range >7.5; however, the reaction speed was less than 15% of that in the tris-HCl buffer. Phosphate inhibited the enzyme. Example 5: Optimum reaction temperature Reaction batches with 2.95 ml 10 mM N-acetyl-L-proline in 0.1 M tris-HCl buffer pH 7.5 were pretempered 10 minutes at temperatures between 22° C. and 85° C. and then the reaction was started by the addition of 0.05 ml acylase. After 5 minutes reaction time, the enzyme activity was determined by ninhydrin determination of the L-proline formed.

The maximum reaction speed was reached at 65° C. and was higher by a factor of 2.3 than at the standard temperature of 30° C.

EXAMPLE 6

Stability of N-acyl-L-proline acylase a) pH stability

The pH stability of N-acyl-L-proline acylase was investigated in the pH range from 4.2 to 10.4. FPLC/Mono Q purified enzyme was diluted tenfold with various 0.1 M buffers with different pH'es and stored 3 weeks at 22° C. Specimens (0.2 ml) were taken at different times and their enzyme activity determined at 30° C. in a reaction batch with the following composition:

| 10 mM | N-acyl-L-proline in 0.1 M tris-HCl buffer pH 7.5 | 2.8 ml |
| | Acylase (1:10 diluted) | 0.2 ml |

As is apparent from Table 11, the enzyme was rapidly inactivated by citrate whereas no appreciable loss of activity was detected during storage in tris-HCl buffer and Na carbonate buffer between pH 7.4 and 10.4.

TABLE 11 pH stability of N-acyl-L-proline acylase

| Buffer | Residual activity (%) after | | | | |
|---|---|---|---|---|---|
| | 1 day | 3 days | 1 week | 2 weeks | 3 weeks |
| Na acetate | | | | | |
| pH 4.2 | 65 | 56 | 34 | 22 | 16 |
| pH 4.6 | 59 | 58 | 49 | 38 | 28 |
| pH 5.2 | 73 | 75 | 64 | 71 | 81 |
| Na citrate | | | | | |
| pH 5.0 | 14 | 1 | 0 | 0 | 0 |
| pH 5.5 | 16 | 3 | 1 | 0 | 0 |
| pH 6.0 | 21 | 5 | 3 | 5 | 3 |
| K phosphate | | | | | |
| pH 6.0 | 82 | 96 | 68 | 48 | 30 |
| pH 6.5 | 84 | 96 | 67 | 52 | 40 |
| pH 7.0 | 86 | 97 | 72 | 63 | 49 |
| pH 7.5 | 88 | 98 | 69 | 56 | 48 |
| Tris-HCl | | | | | |
| pH 7.4 | 82 | 101 | 97 | 145 | 156 |
| pH 8.0 | 107 | 110 | 107 | 163 | 171 |
| pH 8.5 | 117 | 129 | 123 | 166 | 162 |
| pH 9.0 | 101 | 128 | 122 | 160 | 1 |
| Na carbonate | | | | | |
| pH 8. | 93 | 109 | 101 | 133 | 127 |
| pH 9.3 | 93 | 101 | 98 | 65 | 38 |
| pH 9.9 | 98 | 107 | 102 | 134 | 108 |
| pH 10.4 | 121 | 132 | 115 | 128 | 111 | b) Temperature stability

The acylase, dissolved in 0.1 M tris-HCl buffer pH 7.5, was incubated for 30 minutes at temperatures of 20° C. to 85° C. Thereafter, the enzyme activity was determined at 30° C. in a reaction batch with the following composition:

| 10 mM | N-acetyl-L-proline in 0.1 M tris-HCl buffer pH 7.5 | 2.95 ml |
| | Acylase | 0.05 ml |

After 30 minutes of incubation at 70° C., no loss of activity of the enzyme was detected; however, the enzyme was rapidly deactivated at higher temperatures.

EXAMPLE 7

Influences of inhibitors and activators

The influence of various chemical agents as well as metal cations and anions on the reaction speed of the hydrolytic splitting of N-acetyl-L-proline was determined at 30° C. in a reaction batch with the following composition:

| 30 mM | N-acetyl-L-proline in 0.1 M tris-HCl buffer pH 7.0 | 1.0 ml |
| 3 and 30 mM | inhibitor in the above-indicated buffer | 1.0 ml |
| 0.1 M | tris-HCl buffer pH 7.0 | 0.95 ml |
| | acylase | 0.05 ml | a) Influence of various chemical agents

Table 12 shows that 1,10-phenanthroline, 2-mercaptoethanol, 4-chloromercuribenzoate and 4-hydroxymercuribenzoate significantly inhibit the acylase. The enzyme was pre-incubated for 10 minutes at 30° C. with the compound before the addition of substrate to start the reaction.

TABLE 12

Influence of various chemical agents on the acylase activity

| Chemical Agent | Concentration (mM) | Activity (%) |
|---|---|---|
| No agent | — | 100 |
| EDTA | 1 | 101 |
| | 10 | 99 |
| Na citrate | 1 | 102 |
| | 10 | 102 |
| 2,2-bipyridine | 1 | 102 |
| | 10 | 66 |
| 1,10 phenanthroline | 1 | 27 |
| | 10 | 1 |
| Dithiothreitol | 1 | 129 |
| | 10 | 48 |
| Glutathione | 1 | 116 |
| | 10 | 135 |
| 2-mercaptoethanol | 1.4 | 42 |
| | 14 | 14 |
| 4-chloromercuribenzoate | 1 | 85 |
| | 10 | 48 |
| 4-hydroxymercuribenzoate | 1 | 88 |
| | 10 | 41 |
| Iodoacetamide | 1 | 104 |
| | 10 | 101 |
| Iodoacetate | 1 | 97 |
| | 10 | 77 |
| Semicarbazide | 1 | 109 |
| | 10 | 95 |
| PMSF | 0.1 | 104 |
| | 1 | 130 | b) Influence of various metal cations

It is apparent from Table 13 that the native enzyme was not activated by any of the metal cations tested. $Cd^{2+}$, $Cu^{2+}$, $Fe^{2+}$, $Hg^{2+}$, $Sn^{2+}$ and $Zn^{2+}$ hd an inhibiting action. The enzyme was pre-incubated for 10 minutes at 30° C. with the agent before the substrate was added to start the reaction. Table 13: Influence of various cations on the acylasea activity

TABLE 13

| Agent | Concentration (mM) | Activity(%) |
|---|---|---|
| No agent | — | 100 |
| $BaCl_2$ | 1 | 100 |
|  | 10 | 99 |
| $CaCl_2$ | 1 | 100 |
|  | 10 | 91 |
| $CdCl_2$ | 1 | 89 |
|  | 10 | 65 |
| $CoCl_2$ | 1 | 103 |
|  | 10 | 92 |
| $CuSO_4$ | 1 | 61 |
|  | 10 | 19 |
| $FeSO_4$ | 1 | 20 |
|  | 10 | n.bd |
| $FeCl_3$ | 1 | 83 |
|  | 10 | 58 |
| $HgCl_2$ | 1 | 67 |
|  | 10 | 9 |
| $MgCl_2$ | 1 | 106 |
|  | 10 | 99 |
| $MnCl_2$ | 1 | 104 |
|  | 10 | 103 |
| $Ni(NO_3)_2$ | 1 | 94 |
|  | 10 | 75 |
| $SnCl_2$ | 1 | 72 |
|  | 10 | 55 |
| $SrCl_2$ | 1 | 104 |
|  | 10 | 100 |
| $ZnSO_4$ | 1 | 77 |
|  | 10 | 32 |

*n.d. = not determined c) influence of various anions

It is apparent from Table 14 that the acylase was sharply inhibited by phosphate and slightly inhibited by carbonate and nitrite. The inhibiting mechanism of phosphate was non-competitive. The enzyme was pre-incubated 10 minutes at 30° C. with the agent before the substrate was added to start the reaction. The concentration of the anions was 10 mM in each instance.

TABLE 14

| Influence of various anions on the acylase activity | |
|---|---|
| Agent | Activity (%) |
| no agent | 100 |
| NaCl | 99 |
| $Na_2CO_3$ | 75 |
| $NaH_2PO_4$ | 6 |
| $Na_2SO_4$ | 96 |
| $NaNO_2$ | 71 |
| $KNO_3$ | 96 | d) Influence of various cations on the 1,10-phenanthroline-inactivated acylase (apoenzyme FPLC/Mono Q purified enzyme was incubated for 24 hours at 4° C. in the presence of 1 mM 1,10-phenanthroline. Subsequently, enzyme and the chelating agent 1,10-phenanthroline were separated by gel filtration via Sephadex G-25 M (PD-10, firm Pharmacia / LKB, Uppsala, Sweden). The enzyme-containing fractions were combined and the activity determined without and in the presence of various cations (1 mM).

Table 15 shows that the 1,10-phenanthroline-inactivated acylase (apoenzyme) was reactivated by $Co^{2+}$ and $Zn^{2+}$ to 80% and 54% respectively of the initial activity. As has already been described under a), $Cu^{2+}$, $Fe^{2+}$, $Fe^{3+}$, $Hg^{2+}$ and $Sn^{2+}$ inhibited. This indicates that the N-acyl-L-proline acylase is a cobalt- dependent or zinc-dependent metalloenzyme.

TABLE 15

| Influence of various cations on the 1,10-phenanthroline-inactivated acylase | | |
|---|---|---|
| Enzyme preparation | Agent | Activity (%) |
| Native enzyme | — | 100 |
| Inactivated enzyme (before gel filtration) | — | 2 |
| Inactivated enzyme (after gel filtration) | none | 21 |
|  | $BaCl_2$ | 18 |
|  | $CaCl_2$ | 17 |
|  | $CdCl_2$ | 20 |
|  | $CoCl_2$ | 80 |
|  | $CuSO_4$ | 6 |
|  | $FeSO_4$ | 12 |
|  | $FeCl_3$ | 5 |
|  | $HgCl_2$ | 6 |
|  | $MgCl_2$ | 25 |
|  | $MnCl_2$ | 23 |
|  | $Ni(NO_3)_2$ | 21 |
|  | $SnCl_2$ | 10 |
|  | $SrCl_2$ | 23 |
|  | $ZnSO_4$ | 54 |

EXAMPLE 8

Determination of the molecular weight and of the number and size of the sub-units The molecular weight of the natural enzyme was determined by means of gel filtration on Superose 12 HR 10/30. The column (1.0×30 cm) coupled to an FPLC system (firm Pharmacia/LKB, Uppsala, Sweden) was operated at a flow rate of 0.3 ml per minute and 0.2 ml of the FPLC/Mono Q purified enzyme served as specimen. Aprotinin, chymotrypsinogen A, aldolase, catalase and ferritin were used as calibrating proteins. The molecular weight of N-acyl-L-proline acylase is 380,000±40,000 daltons.

The size and number of the subunits of the enzyme were determined by means of gel electrophoresis in the presence of sodium dodecylsulfate (SDS). The molecular weight of the subunits is 45,000±5,000 daltons. That means that the N-acyl-L proline acylase consists of 8 subunits of identical size. Phosphorylase b (rabbit muscle), albumin (bovine serum), ovalbumin (egg albumin), carboanhydrase (bovine erythrocytes) and trypsin inhibitor (soybean) were used for the calibration curve.

EXAMPLE 9

Dependence of the acylase activity on the substrate concentration

The dependence of the reaction speed of the hydrolytic splitting of acetic acid from the compound N-acetyl-L-proline in the presence of N-acyl-L-proline acylase was determined in a reaction batch with the following composition:

| | |
|---|---|
| N-acetyl-L-proline in 0.1M tris-HCl buffer—pH 7.0 | 1.0 ml |
| 0.1M tris-HCl buffer—pH 7.0 | 1.95 ml |
| Acylase | 0.05 ml |

The reaction temperature was 30° C. and the incubation time 10 minutes. The N-acetyl-L-proline concentration of the reaction batch was varied in a range from 1 to 50 mM. The $K_M$ value for N-acetyl-L-proline is 5 mM under the conditions indicated above.

EXAMPLE 10

Substrate specificity of N-acyl-L-proline acylase a) Hydrolysis of various N-acetyl-L-amino acids and N-chloroacetyl-L-amino acids The activity of acylase was determined with various N-acetyl-L-amino acids and N-chloroacetyl-L-amino acids in a reaction batch with the following composition:

| 20 mM | N-acetyl-amino acid or N-chloroacetyl amino acid | 1.0 ml |
|---|---|---|
| 0.1M | Tris-HCl buffer pH 7.0 | 0.95 ml |
| | Acylase | 0.05 ml |

The reaction temperature was 30° C. and the incubation time 15 minutes to 24 hours. 0.2 ml samples of the reaction batch in each instance were mixed at different times with 0.2 ml 10% (w/v) trichloroacetic acid and the denatured protein centrifuged off for 10 minutes at 11,000 rpms in a table centrifuge. The supernatant was diluted with a 0.1 M Na citrate buffer pH 2.2 with 25% (v/v) 2.2-thiodiethanol and 0.1% (v/v) phenol 1 : 5 and 1 : 50 respectively. The amino acids released were quantitatively detected by an amino-acid analyzer LC 5001 of the firm Biotronic, Maintal, Federal Republic of Germany. In Table 16, the substrates marked with * and the corresponding products were quantified by means of HPLC.

For the determination of the relative activities, the hydrolysis rate with N-acetyl-L-proline under comparable reaction conditions was set equal to 100%.

As can be seen from Table 16, N-acetyl- and N-chloroacetyl-L-proline, N-chloroacetyl-L-thiazolidine-4-carboxylic acid and N-chloroacetyl-DL-thiazolidine-2-carboxylic acid were hydrolyzed especially well. In addition, N-chloroacetyl-D,L-pipecolic acid, N-chloroacetyl-L-methionine, N-chloroacetyl-L-valine and N-acetyl-L-alanine were also reacted at a distinctly lower speed.

TABLE 16

Specificity of N-acyl-L-proline acylase in relation to various N-acetyl- and N-chloroacetyl amino acids

| Substrate | Rel. activity (%) |
|---|---|
| Ac-L-Pro | 100 |
| Ac-L-Ala | 9.3 |
| Ac-L-Val | 0.2 |
| Ac-D,L-Ser | 0.2 |
| Ac-L-Cys | 0 |
| Ac-L-Tyr | 0 |
| ClAc-L-Pro | 362 |
| ClAc-L-thiazolidine-4-carboxylic acid | 462 |
| ClAc-D,L-thiazolidine-2-carboxylic acid*+ | 202 |
| ClAc-D,L-pipecolic acid*+ | 16 |
| Ac-L-azetidine-2-carboxylic acid* | 0 |
| ClAc-L-indolin-2-carboxylic acid* | 0 |
| ClAc-L-Met | 17.1 |
| ClAc-L-Val | 14.1 |
| ClAc-L-Leu | 1.9 |
| ClAc-L-Phe | 1.0 |
| ClAc-L-Tyr | 1.0 |
| ClAc-L-Ile | 0.5 |
| ClAc-D,L-1-aminocyclohexanoic acid | 0 |

+ The substrate concentration was 50 mM.

b. Hydrolysis of various proline derivatives

The activity of the acylase was determined with various proline derivatives as under a).

To determine the relative activities the hydrolysis rate with N-acetyl-L proline under comparable reaction conditions was set equal to 100%.

As can be seen from Table 17, the acylase is L-specific, because N-acetyl-D-proline was not hydrolized. The enzyme requires the free carboxyl group of the proline as a substrate, because N-acetyl-L-prolineamide and N-acetyl-L-proline methyl ester were not hydrolyzed. N-chloroacetyl-L-proline was about 3.6 times more rapidly hydrolyzed as N-acetyl-L-proline. An approximately 3 to 20 times reduced hydrolysis rate was observed with N-formyl-L-proline, N-propionyl-L-proline, N-butyryl-L-proline, N-valeryl-L-proline, N-caproyl-L-proline, N-acetyl-L-4-hydroxyproline, N-benzoxycabonyl-glycyl-L-proline and glycyl-L-proline.

TABLE 17

Specificity of N-acyl-L-proline-acylase with various proline derivatives

| Substrate | Relative Activity (%) |
|---|---|
| Ac-L-Pro-OH | 100 |
| Ac-D-Pro-OH | 0 |
| ClAc-L-Pro-OH | 362 |
| Ac-L-Pro-NH$_2$ | 0 |
| Ac-L-Pro-OMe | 0 |
| Ac-L-Pro(4-OH)-OH | 10 |
| Ac-L-Ala-L-Pro-OH | 0 |
| Formyl-L-Pro-OH | 18 |
| Propionyl-L-Pro-OH | 29 |
| Butyryl-L-Pro-OH | 14 |
| Valeryl-L-Pro-OH | 15 |
| Caprcyl-L-Pro-OH | 9 |
| Z-L-Pro-OH | 0 |
| Z-D-Pro-OH | 0 |
| Z-L-Pro-NH$_2$ | 0 |
| Z-L-Pro-L-Ala-OH | 0 |
| Z-Gly-L-Pro-OH | 11 |
| Boc-L-Pro-OH | 0 |
| H-Gly-L-Pro-OH | 4 |
| H-L Ala-L-Pro-OH | 0 |
| H-L-Pro-NH$_2$ | 0 |
| H-L-Pro-Gly-OH | 0 |

EXAMPLE 11

Stereospecificity of hydrolysis of N-Acetyl-D,L-Proline with N-acyl-L-proline-acylase The hydrolysis of N-acyl-L-proline, N-acetyl-D,L-proline and N-acetyl-D-proline was determined in the following reaction mixture:

| 20 mM | Substrate in 0.1M Tris-HCl buffer pH 7.0 | 1.0 ml |
|---|---|---|
| 0.1M | Tris-HCl buffer pH 7.0 | 0.95 ml |
| | Acylase | 0.05 ml |

The reaction mixture was incubated for two hours at 30° C. and the L-proline produced was determined by amino acid analysis as in Example 10.

Table 18 Shows that the N-acyl-L-proline acylase hydrolyzes N-acetyl-L-proline but not N-acetyl-D-proline.

TABLE 18

Stereospecificity of N-Acyl-L-proline acylase

| Substrate | Concentration (mmol/l) | L-proline (mmol/l) |
|---|---|---|
| N-acetyl-L-proline | 10 | 10.25 |
| N-acetyl-D,L-proline | 10 | 4.82 |

TABLE 18-continued

Stereospecificity of N-Acyl-L-proline acylase

| Substrate | Concentration (mmol/l) | L-proline (mmol/l) |
|---|---|---|
| N-acetyl-D-proline | 10 | <0.01 |

EXAMPLE 12

Synthesis of N-acetyl-L-proline, N-propionyl-L-proline and N-butyryl-L-proline

The reverse reaction, the synthesis of N-acetyl-L-proline from acetic acid and L-proline was investigated in the following reaction mixture.

| 1M | Sodium acetate + 5M L-proline in 0.1M Tris-HCl buffer pH 7.0 | 1 ml |
|---|---|---|
| | Acylase (FPLC-purified) | 1 ml |

The reaction mixture was incubated at 30° C. Samples were taken at various times, and reacted with a 10% aliquot (w/v) trichloracetic acid and the denatured protein was separated in a table centrifuge at 11,000 rpm. The supernatant was analyzed by HPLC after dilution with the eluent.

After incubation for 7 days, the N-acetyl-L-proline concentration increased to 0.2 mol/liter, corresponding to a yield of 40%, based on the sodium acetate. The control without enzyme gave n N-acetyl-L-proline.

In a similar manner, N-propionyl-L-proline and N-butyryl-L-proline can be made from sodium propionate and sodium butyrate. However, an attempt to synthesize N-benzoyl-L-proline, N-phenylacetyl-L-proline and N-phenylpropionyl-L-proline from sodium benzoate, sodium phenylacetate and sodium phenylpropionate was not successful.

What is claimed is:

1. A substantially purified N-acyl-L-proline acylase, characterized by the following properties:
   1) Reactivity: It splits the acetyl group from N-acetyl-L-proline, creating acetic acid and L proline as final products and it condenses acetic acid and L-proline, creating N-acetyl-L-proline and water as final products:
   2) Substrate specificity: It hydrolyzes N-acetyl-L proline, N-chloroacetyl-L-proline, N-formyl-L-proline, N-propionyl-L-proline, N-butyryl-L-proline, N-valeryl-L-proline, N-caproyl-L-proline, N-acetyl-L-4-hydroxyproline, N-chloroacetyl-L-thiazolidine-4-carboxylic acid, N-chloroacetyl-L-thiazolidine-2-carboxylic acid, N-chloroacetyl-L-pipecolic acid, N-benzyloxycarbonyl-glycyl-L-proline, glycyl-L-proline, N-acetyl-L-alanine, N-chloroacetyl-L-methionine and N-chloroacetyl-L-valine;
   3) Optimum pH: The optimum pH is 6.8±0.5;
   4) pH stability: It exhibits good stability at 22° C. over a period of 3 weeks in a pH range between pH 7.0 and pH 10.0:
   5) Optimum temperature:
   The optimum temperature is 65° C. at a pH of 7.5;
   6) Temperature resistance: No loss of activity can be detected at 70° C. and pH 7.5 after 30 minutes of incubation;
   7) Influences of inhibitors and activators: In particular, 1,10-phenanthroline, 2-mercaptoethanol, 4-chloromercuribenzoate, 4-hydroxymercuribenzoate, $Hg^{2+}$, $Cu^{2+}$, $Fe^{2+}$, $Fe^{3+}$, $Sn^{2+}$, $Zn^{2+}$ and $PO_4^{3-}$ exhibit an inhibiting action and $Co^{2+}$ and $Zn^{2+}$ an activating action on the apoenzyme;
   8) Molecular weight: The molecular weight is 380,000±40,000 daltons;
   9) Subunits: The molecule consists of 8 equally large subunits with 45,000 ±daltons each;
   10) $K_M$ value: The $K_M$ value for the substrate N-acetyl-L-proline is 5 mM (30° C., 0.1 M tris-HCl buffer, pH 7.0).

* * * * *